United States Patent [19]

Holmes

[11] Patent Number: 4,722,927
[45] Date of Patent: Feb. 2, 1988

[54] PYRIMIDINE AMIDES OF OLEIC OR LINOLEIC ACID, COMPOSITION CONTAINING THEM AND THEIR USE AS INHIBITORS OF ACYL-COA CHOLESTEROL ACYLTRANSFERASE

[75] Inventor: Ann Holmes, Dexter, Mich.

[73] Assignee: Warner-Lambert Company, Morris Plains, N.J.

[21] Appl. No.: 856,551

[22] Filed: Apr. 28, 1986

[51] Int. Cl.4 ............... A61K 31/505; C07D 239/42; C07D 239/60
[52] U.S. Cl. .................................. 514/256; 514/269; 514/274; 544/301; 544/311; 544/316; 544/319; 544/322
[58] Field of Search ............... 544/301, 311, 316, 319, 544/322; 514/256, 269, 274

[56] References Cited

FOREIGN PATENT DOCUMENTS 175652 3/1986 European Pat. Off. ............ 544/322

Primary Examiner—Henry R. Jiles
Assistant Examiner—Kurt G. Briscoe
Attorney, Agent, or Firm—Jerry F. Janssen

[57] ABSTRACT

Certain disubstituted pyrimidineamides of oleic and linoleic acids are potent inhibitors of the enzyme acyl-CoA:cholesterol acyltransferase and are thus useful agents for inhibiting the intestinal absorption of cholesterol.

6 Claims, No Drawings

PYRIMIDINE AMIDES OF OLEIC OR LINOLEIC ACID, COMPOSITION CONTAINING THEM AND THEIR USE AS INHIBITORS OF ACYL-COA CHOLESTEROL ACYLTRANSFERASE

BACKGROUND OF THE INVENTION

This invention relates to chemical compounds having pharmacological activity, to pharmaceutical compositions which include these compounds, and to a pharmaceutical method of treatment. More particularly, this invention concerns certain alkyl- and alkyloxysubstituted pyrimidine amides of oleic or linoleic acid which inhibit acyl-coenzyme A:cholesterol acyltransferase (ACAT), pharmaceutical compositions containing these compounds, and a method of inhibiting intestinal absorption of cholesterol.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine.

SUMMARY OF THE INVENTION

The present invention provides a class of compounds with ACAT inhibitory activity having the structure

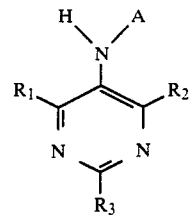

where A is

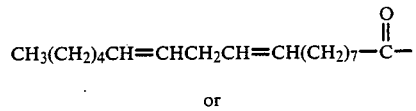

or

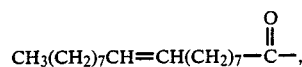

$R_1$, $R_2$, and $R_3$ are independently selected from hydrogen, straight or branched alkyl of from one to four carbon atoms, or straight or branched alkyloxy of from one to four carbon atoms.

By the term "alkyl" as used throughout this specification and the appended claims is meant a branched or unbranched hydrocarbon grouping derived from a saturated hydrocarbon of from one to four carbon atoms by removal of a single hydrogen atom. Examples of alkyl groups contemplated as falling within the scope of this invention include methyl, ethyl, propyl, 1-methylethyl, butyl, 1-methylpropyl, 2-methylpropyl, and 1,1-dimethylethyl.

By the term "alkyloxy" is meant an alkyl group, as defined above, attached to the parent molecular moiety through an oxygen atom.

Preferred compounds of the present invention are those in which $R_1$, and $R_2$ are lower alkyloxy. Most preferred are the compounds (Z)-N-(4,6-dimethoxy-5-pyrimidinyl)-9-octadecenamide and (Z)-N-(4,6-diethoxypyrimidinyl)-9-octadecenamide.

The compounds of the present invention are prepared by reacting 9-octadecenoyl chloride (oleic acid chloride) or 9,12-octadecadienoyl chloride (linoleic acid chloride) with the desired substituted 5-aminopyrimidine in a polar solvent such as tetrahydrofuran, chloroform, dimethylformamide, and the like in the presence of a tertiary amine acid scavenger such as triethylamine.

The reaction may be carried out at any temperature between room temperature and the boiling point of the solvent, with room temperature being preferred.

The reaction is allowed to proceed until analysis of the mixture by a means such as chromatography indicates substantially complete reaction between the acid chloride and the substituted 5-aminopyrimidine. Reaction times may vary between about two hours to about 24 hours, depending upon the particular reagents and reaction temperature employed. Starting materials are known or, if not previously known, are prepared by methods well known in the art.

As shown by the data presented below in Table 1, the compounds of the present invention are potent inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the inhibition of intestinal absorption of dietary cholesterol or the reabsorption of cholesterol released into the intestine by normal body action.

In Vitro Tests

The ability of representative compounds of the present invention to inhibit ACAT was measured using an in vitro test more fully described in Field, F. J. and Salone, R. G., *Biochemica et Biophysica* 712: 557-570 (1982). The test assesses the ability of a test compound to inhibit the acylation of cholesterol by oleic acid by measuring the amount of radio-labeled cholesterol oleate formed from radio-labeled oleic acid in a tissue preparation containing rabbit intestinal microsomes.

The data appear in Table 1 where they are expressed as $IC_{50}$ values; i.e. the concentration of test compound required to inhibit 50% expression of the enzyme.

TABLE 1

| Compound | $IC_{50}$ (Micromolar) |
| --- | --- |
| (Z)-N—(4,6-dimethoxy-5-pyrimidinyl)-9-octadecenamide | 0.20 |
| (Z)-N—(4,6-diethoxy-5-pyrimidinyl)-9-octadecenamide | 0.53 |

In Vivo Tests

Male, New Zealand white rabbits weighing approximately 1 kg are fed a normal diet of 40 g per day of rabbit chow (Purina No. 5321, Ralston Purina Co., 711 West Fuesser Road, Mascoutah, Illinois, 62224, USA). After six days on this diet, the rabbits are fed 50 g per day for three days of a cholsterol-enriched diet consisting of one part of a cholesterol-containing chow (Purina Catalog No. 841206WLI, 0.25% cholesterol) and two parts of normal chow. Next, the rabbits are fed 60 g per day for four days of a cholsterol-enriched diet consisting of two parts of a cholesterol-containing chow (Purina Catalog No. 841206WLI, 0.25% cholesterol) and one part of normal chow.

After this meal adaptation and cholesterol loading period, the test compounds are administered to the test animals in oral doses of 50 mg/kg of body weight thirty minutes prior to each meal for seven days. Control animals are administered vehicle only.

The animals are sacrificed three hours after their last meal in the postabsorptive state and serum cholesterol levels are then determined for each animal.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as agents for the inhibition of intestinal absorption of cholesterol, the compounds utilized in the pharmaceutical method of this invention are administered to the patient at dosage levels of from 500 to 2000 mg per day. For a normal human adult of approximately 70 kg of body weight, this translates into a dosage of from 7 to 30 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

The following preparative examples are provided to enable one skilled in the art to practice the invention, and are illustrative thereof. They are not to be read as limiting the scope of the invention as it is defined by the appended claims.

EXAMPLE 1

Preparation of (4,6-Dimethoxy-5-pyrimidinyl)-9-octadeceneamide 4,6-Dimethoxy-5-aminopyrimidine (4.65 g, 0.03 mol) and 4.15 ml (3.03 g, 0.03 mole) of triethylamine were dissolved in 100 ml of tetrahydrofuran. To this mixture was added, with stirring, a solution of 12.03 g (0.03 mol) of oleic acid chloride (75%) dissolved in 200 ml of tetrahydrofuran.

The mixture was stirred at room temperature overnight, after which the solution was filtered and the filtrate concentrated under vacuum. Water was added to the residue, and the resulting oil was taken up in ethyl acetate. This solution was washed successively with 2M aqueous hydrochloric acid, sodium bicarbonate solution, and water. The organic layer was separated, dried over andhydrous magnesium sulfate and evaporated.

The resulting oil solidifided to a wax which was chromatographed on silica, eluting with 50:50 ethyl acetate:hexane (volume/volume). Recrystalization from isopropyl ether/hexane yielded 7.4 g of (4,6-dimethoxy-5-pyrimidinyl)-9-octadecenamide, mp 95°-96° C.

Analysis for $C_{24}H_{41}N_3O_3$: Calc.: C, 68.69%; H, 9.85%; N, 10.01%; Found: C, 68.83%; H, 9.87%; N, 10.12%.

EXAMPLE 2

Preparation of (4,6-Diethoxy-5-pyrimidinyl)-9-octadecenamide

Employing the method of Example 1, but using 4,6-diethoxy-5-amino pyrimidine, 13.8 g of the title compound were obtained as a wax.

Analysis for $C_{26}H_{45}N_3O_3$: Calc.: C, 69.75; H, 10.13; N, 9.39; Found: C, 70.19; H, 10.26; N, 8.81.

We claim:

1. A compound having the formula

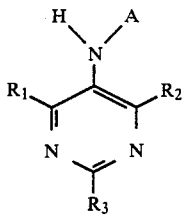

wherein A is

or

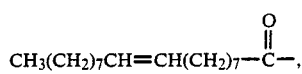

$R_1$, $R_2$, and $R_3$ are independently selected from hydrogen, straight or branched alkyl of from one to four carbon atoms, or straight or branched alkyloxy of from one to four carbon atoms.

2. A compound as defined in claim 1 wherein $R_1$ and $R_2$, are independently lower alkyloxy of from one to four carbon atoms.

3. A as defined in claim 2 having the name (Z)-N-(4,6-dimethoxypyrimidinyl)-9-octadecenamide.

4. A as defined in claim 2 having the name (Z)-N-(4,6-diethoxypyrimidinyl)-9-octadecenamide.

5. A pharmaceutical composition useful for inhibiting the intestinal absorption of cholesterol comprising an ACAT-inhibitory effective amount of a compound as defined by claim 1 in combination with a pharmaceutically acceptable carrier.

6. A method of inhibiting intestinal absorption of cholesterol comprising administering to a patient an ACAT-inhibitory effective amount of a compound as defined by claim 1 in combination with a pharmaceutically acceptable carrier.

* * * * *